United States Patent [19]
Van Gemert et al.

[11] Patent Number: 5,552,090
[45] Date of Patent: Sep. 3, 1996

[54] PHOTOCHROMIC NAPHTHOPYRAN COMPOUNDS

[75] Inventors: Barry Van Gemert, Murrysville; David B. Knowles, Apollo, both of Pa.

[73] Assignee: PPG Industries, Inc., Pittsburgh, Pa.

[21] Appl. No.: 359,773

[22] Filed: Dec. 20, 1994

Related U.S. Application Data

[60] Continuation-in-part of Ser. No. 302,292, Sep. 8, 1994, Pat. No. 5,458,815, which is a division of Ser. No. 80,250, Jun. 21, 1993, Pat. No. 5,384,077.

[51] Int. Cl.$^6$ .............. G02B 5/23; G02B 27/00; C07D 405/10; C07D 413/10
[52] U.S. Cl. ............ 252/586; 549/389; 548/962; 548/950; 548/525; 548/454; 546/201; 546/196; 546/167; 546/277.4; 544/315; 544/150; 544/127; 540/524; 524/106; 524/105; 524/104; 524/100
[58] Field of Search ............ 549/389; 548/962, 548/950, 525, 454, 374, 356, 336, 300; 546/201, 196, 167, 273; 544/375, 150, 127; 540/524; 524/106, 105, 104, 100, 99, 97, 96, 93, 92, 110, 94; 252/586

[56] References Cited

U.S. PATENT DOCUMENTS

| | | | |
|---|---|---|---|
| 3,562,172 | 2/1971 | Ono et al. | 252/300 |
| 3,567,605 | 3/1971 | Becker | 204/158 |
| 3,578,602 | 5/1971 | Ono et al. | 252/300 |
| 3,627,690 | 12/1971 | Casella et al. | 252/300 |
| 4,215,010 | 7/1980 | Hovey et al. | 252/300 |
| 4,342,668 | 8/1982 | Hovey et al. | 252/586 |
| 4,637,698 | 1/1987 | Kwak et al. | 351/163 |
| 4,720,356 | 1/1988 | Chu | 252/586 |
| 4,816,584 | 3/1990 | Kwak et al. | 544/71 |
| 4,818,096 | 4/1988 | Heller et al. | 351/163 |
| 4,826,977 | 5/1989 | Heller et al. | 544/70 |
| 5,066,818 | 11/1991 | Van Gemert | 549/389 |
| 5,200,116 | 4/1993 | Heller | 252/586 |
| 5,238,981 | 8/1993 | Knowles | 524/110 |
| 5,244,602 | 9/1993 | Van Gemert | 252/589 |
| 5,274,132 | 12/1993 | Van Gemert | 549/389 |
| 5,340,857 | 8/1994 | Van Gemert . | |
| 5,369,158 | 11/1994 | Knowles . | |

FOREIGN PATENT DOCUMENTS 816719  8/1937  France .

OTHER PUBLICATIONS

George A. Olah, *Friedel–Crafts and Related Reactions*, Interscience Publishers, vol. 3, Chap. XXXI, pp. 1–8, 82–88, 1964.
"Regioselective Friedel–Crafts Acylation of 1,2,3,4–Tetrahydroquinoline and Related Nitrogen Hetercycles", Ishihara, Yugi et al., J. Chem. Soc., Berkin Trans. 1, pp. 3401–3406, 1992.
R. C. Elderfield, *Heterocyclic Compounds*, 1951, vol. 2, Chapters 3 and 5, pp. 123–144, pp. 164–172.
*Organic Reactions*, vol. II, Chapter 1, "The Claisen Rearrangement" by D. Stanley Tarbell, pp. 26–27, R. Adams, Editor, John Wiley and Sons, Inc., 1944.

*Primary Examiner*—Nicky Chan
*Attorney, Agent, or Firm*—Frank P. Mallak; Irwin M. Stein

[57] ABSTRACT

Described are novel reversible photochromic naphthopyran compounds, examples of which are compounds substituted at the 3 position of the pyran ring with (i) an aryl substituent and (ii) a phenyl substituent having a 5- or 6-member heterocyclic ring fused at the number 3 and 4 carbon atoms of the phenyl substituent, and at the 6 position of the naphthyl portion of the naphthopyran compound with a nitrogen-containing heterocyclic ring. Also described are organic host materials that contain or that are coated with such compounds. Articles such as ophthalmic lenses or other plastic transparencies that incorporate the novel naphthopyran compounds or combinations thereof with complementary photochromic compounds, e.g., spiro(indoline) type compounds, are also described.

21 Claims, No Drawings

PHOTOCHROMIC NAPHTHOPYRAN COMPOUNDS

CROSS REFERENCE TO RELATED APPLICATIONS

This application is a continuation in part of application Ser. No. 08/302,292 filed Sep. 8, 1994, now U.S. Pat. No. 5,458,815, which is a division of application Ser. No. 08/080,250 filed Jun. 21, 1993, now U.S. Pat. No. 5,384,077.

DESCRIPTION OF THE INVENTION

The present invention relates to certain novel naphthopyran compounds. More particularly, this invention relates to novel photochromic naphthopyran compounds and to compositions and articles containing such novel naphthopyran compounds. When exposed to light radiation involving ultraviolet rays, such as the ultraviolet radiation in sunlight or the light of a mercury lamp, many photochromic compounds exhibit a reversible change in color. When the ultraviolet radiation is discontinued, such a photochromic compound will return to its original color or colorless state.

Various classes of photochromic compounds have been synthesized and suggested for use in applications in which a sunlight-induced reversible color change or darkening is desired. U.S. Pat. No. 3,567,605 (Becker) describes a series of pyran derivatives, including certain benzopyrans and naphthopyrans. These compounds are described as derivatives of chromene and are reported to undergo a color change, e.g., from colorless to yellow-orange, on irradiation by ultraviolet light at temperatures below about −30° C. Irradiation of the compounds with visible light or upon raising the temperature to above about 0° C. is reported to reverse the coloration to a colorless state.

The present invention relates to novel naphthopyran compounds whose colored forms have been found to have an unexpectedly higher absorption maxima than corresponding compounds having no substituents or different substituents at the same ring position. These compounds are substituted at the 3 position of the pyran ring with (i) an aryl substituent and (ii) a phenyl substituent having a 5- or 6-member oxygen and/or nitrogen containing heterocyclic ring fused at the number 3 and 4 carbon atoms of the phenyl substituent, and at the 6 position of the naphthyl portion of the naphthopyran compound with a nitrogen-containing heterocyclic ring.

DETAILED DESCRIPTION OF THE INVENTION

In recent years, photochromic plastic materials, particularly plastic materials for optical applications, have been the subject of considerable attention. In particular, photochromic ophthalmic plastic lenses have been investigated because of the weight advantage they offer, vis-a-vis, glass lenses. Moreover, photochromic transparencies for vehicles, such as cars and airplanes, have been of interest because of the potential safety features that such transparencies offer.

Compounds, such as 3,3-diphenyl-3H-naphtho-[2,1-b]pyran, change color on exposure to the near ultraviolet; but, at room temperature and above, this compound bleaches too rapidly for use in an ophthalmic lens. Substitution of either or both of the phenyl rings at the meta or para positions result in an even more rapid bleach rate, and therefore an even lower color intensity. The compound, 2,2-diphenyl-2H-naphtho[1,2-b]pyran, also colors on exposure to near ultraviolet light at room temperature but does not bleach in a reasonable period of time. Substitution of either or both of the phenyl rings at the meta or para positions have little effect on the rate of bleaching of these compounds.

In accordance with the present invention, it has now been discovered that certain novel naphthopyran compounds having a high quantum efficiency for coloring in the near ultraviolet and an acceptable rate of fade may be prepared. These compounds may be described as naphthopyrans substituted at the 3 position of the pyran ring with (i) an aryl substituent and (ii) a phenyl substituent having a 5- or 6-member oxygen and/or nitrogen containing heterocyclic ring fused at the number 3 and 4 carbon atoms of the phenyl substituent and with a nitrogen-containing heterocyclic ring at the 6 position of the naphthyl portion of the naphthopyran compound. These compounds may be represented by the following graphic formula:

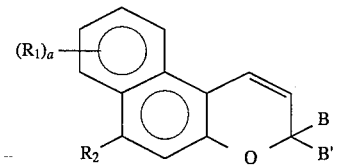

In graphic formula I, $R_1$ may be $C_1$–$C_{10}$ alkyl, halogen, or the group, —O—L, wherein L is a $C_1$–$C_{12}$ alkyl, e.g., methyl, ethyl, propyl, butyl, pentyl, hexyl, heptyl, octyl, nonyl, decyl, undecyl, and dodecyl, said halogen being chloro, fluoro, or bromo, and a is the integer 0, 1 or 2. Preferably, $R_1$ is $C_1$–$C_5$ alkyl, fluoro, bromo or the group, —O—L, wherein L is $C_1$–$C_4$ alkyl and a is the integer 0 or 1. Most preferably, $R_1$ is $C_1$–$C_3$ alkyl, fluorine or the group —O—L, wherein L is methyl, and a is the integer 0 or 1.

In graphic formula I, $R_2$ may be a saturated, unsubstituted or mono- or di-substituted nitrogen containing heterocyclic group selected from the following groups represented by graphic formulae IA through IG:

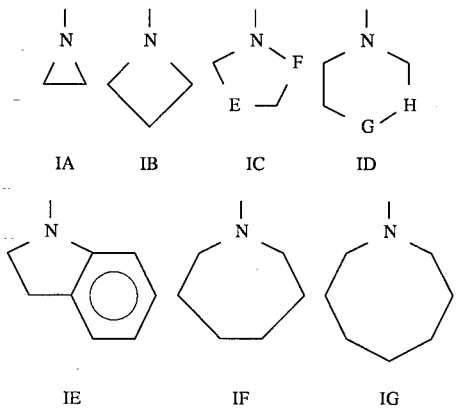

wherein E and F in graphic formula IC, are each a nitrogen or carbon atom, provided that when E is nitrogen, F is carbon atom, and G in graphic formula ID, is a nitrogen, oxygen, or carbon atom and H is a nitrogen or carbon atom, provided that when H is nitrogen, G is a carbon atom. Examples of $R_2$ groups include aziridino, azetidino, 1-pyrrolidyl, 1-pyrrolinyl, 1-imidazolidyl, 2-imidazolin-1-yl, 2-pyrazolidyl, 3-pyrazolin-2-yl, morpholino, piperidino, piperazinyl, 4-methyl-1-piperazinyl, 1,4,5,6,-tetrahydropyrimidinyl, 1-indolinyl, hexamethyleneimino, and heptamethyleneimmino. The substituents for $R_2$ can be $C_1$–$C_6$ alkyl and/or $C_1$–$C_6$ alkoxy. Preferably, $R_2$ is an unsubstituted or mono-substituted member of the group consisting of indolinyl, morpholino, and piperidino. More preferably, $R_2$ is morpholino.

B may be the substituted or unsubstituted aryl group, naphthyl or phenyl, said aryl substituents being $C_1$–$C_5$ alkyl, halo($C_1$–$C_5$)alkyl, hydroxy, $C_1$–$C_5$ alkoxy, $C_1$–$C_4$ alkoxy($C_1$–$C_4$)alkyl, halogen, morpholino, piperidino, or R (R')N—, wherein R and R' are each hydrogen or $C_1$–$C_3$ alkyl, said halogen (or halo) groups being fluoro or chloro Preferably, B is represented by the following graphic formula II:

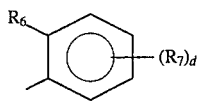

In graphic formula II, $R_6$ is hydrogen, $C_1$–$C_4$ alkyl, $C_1$–$C_4$ alkoxy, fluoro, or chloro and each $R_7$ is a $C_1$–$C_4$ alkyl, $C_1$–$C_4$ alkoxy, hydroxy, chloro, or fluoro and d is an integer from 0 to 2. Preferably, $R_6$ is hydrogen and $R_7$ is selected from the group consisting of fluoro, methyl and methoxy.

B' may be represented by one of the following graphic formulae III or IV:

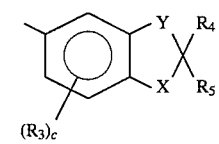

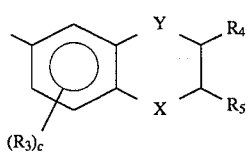

In graphic formula III and IV, X is oxygen or nitrogen and Y is carbon or oxygen, provided that when X is nitrogen, Y is carbon; $R_4$ and $R_5$ are each hydrogen or $C_1$–$C_5$ alkyl; each $R_3$ is a $C_1$–$C_5$ alkyl, $C_1$–$C_5$ alkoxy, hydroxy, or halogen, said halogen substituent being chloro, fluoro, or bromo, and c is an integer from 0 to 3, e.g., 0, 1, 2, or 3. Preferably, B' is represented by graphic formula III or IV, wherein X is oxygen; Y is carbon or oxygen; $R_4$ and $R_5$ are each hydrogen or $C_1$–$C_4$ alkyl; each $R_3$ is a $C_1$–$C_4$ alkyl, $C_1$–$C_4$ alkoxy, hydroxy, or fluoro; and c is the integer 0, 1, or 2. Most preferably, B' is 2,3-dihydroxybenzofuran-5-yl, 2-methyldihydroxybenzofuran-5-yl, indoline-5-yl, 1,2,3,4-tetrahydroquinoline-6-yl, chroman-6-yl, or 1,3-benzodioxole-5-yl.

In graphic formula III, when $R_4$ and $R_5$ are H and when X is oxygen and Y is carbon and c is zero, the group is a 2,3-dihydrobenzofuran-5-yl; when X is oxygen and Y is oxygen and c is zero, the group is 1,3-benzodioxole-5-yl; and when X is nitrogen and Y is carbon and c is zero, the group is indoline-5-yl. In graphic formula IV, when X is oxygen and Y is carbon, the unsubstituted group is a chroman-6-yl; when X is oxygen and Y is oxygen, the unsubstituted group is a 1,4-benzodioxan-6-yl; and when X is nitrogen and Y is carbon, the unsubstituted group is 1,2,3,4-tetrahydroquinoline-6-yl. For brevity, these groups will be referred to herein as fused heterocyclic-phenyl groups.

Compounds represented by graphic formula I are prepared by the sequence outlined in Reactions A through D.

Compounds represented by graphic formula I are prepared by Friedel-Crafts methods using an appropriately substituted or unsubstituted benzoyl chloride of graphic formula V with a commercially available 5-member heterocyclic-fused benzene compound, such as 2,3-dihydrobenzofuran benzodioxole represented by graphic formula VI. See the publication *Friedel-Crafts and Related Reactions,* George A. Olah, Interscience Publishers, 1964, Vol. 3, Chapter XXXI (Aromatic Ketone Synthesis), and "Regioselective Friedel-Crafts Acylation of 1,2,3,4-Tetrahydroquinoline and Related Nitrogen Heterocycles: Effect on NH Protective Groups and Ring Size" by Ishihara, Yugi et al, J. Chem. Soc., Perkin Trans. 1, pages 3401 to 3406, 1992. If a 5-member heterocyclic-fused benzene compound containing an oxygen is not commercially available, it may be prepared by methods well known in the literature, for example, from an appropriately substituted phenol as described in *Organic Reactions,* Vol. II, pages 26 and 27.

In Reaction A, the compounds represented by graphic formulae V and VI are dissolved in a solvent, such as carbon disulfide or methylene chloride, in the presence of a Lewis acid, such as aluminum chloride, to form the corresponding heterocyclic fused benzophenone represented by graphic formula VII.

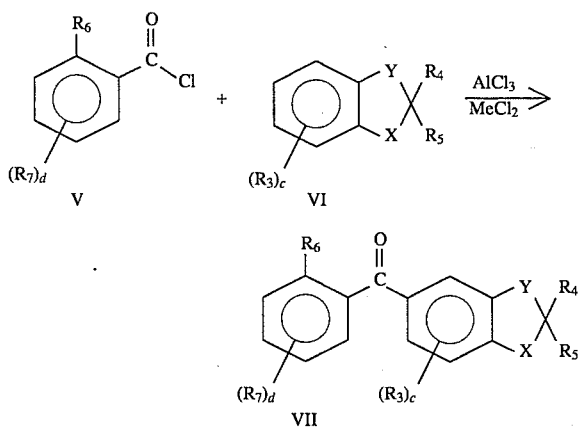

In Reaction B, the heterocyclic fused benzophenone represented by graphic formula VII is reacted with sodium acetylide in a suitable solvent, such as dry tetrahydrofuran, to form the corresponding propargyl alcohol represented by graphic formula VIII.

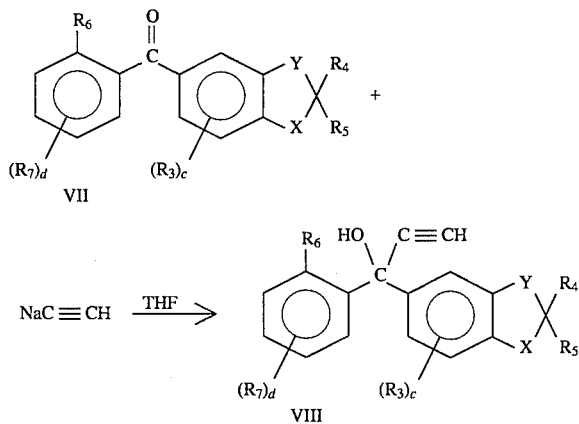

In Reaction C, the propargyl alcohol represented by graphic formula VIII is coupled with the appropriately substituted 2-naphthol, represented by graphic formula IX, in an inert solvent such as toluene in the presence of an acid catalyst such as dodecylbenzene sulfonic to form the naphthopyrans of graphic formula X, which are a subset of compounds represented by graphic formula I. By substituting the 5-member heterocyclic fused benzene compound of graphic formula VI with a 6-member heterocyclic fused benzene compound, such as 1,4-benzodioxan, chroman, etc., in reaction A, compounds similar to those represented by graphic formula X may be prepared except they would contain a 6-member heterocyclic ring fused at the number 3 and 4 carbon atoms of the 3-phenyl substituent.

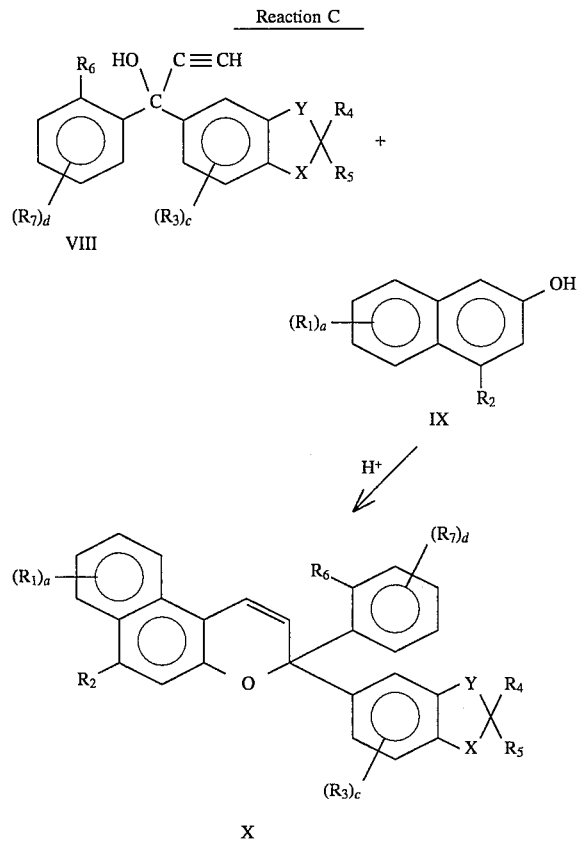

In Reaction D, the $R_2$ substituted 2-naphthols represented by graphic formula IX are prepared in a two step sequence. In Step 1, the potassium salt of 1,2-naphthoquinone- 4-sulfonic acid, represented by graphic formula XI, is slurried in water and an equivalent of a cyclic secondary amine, represented by $R_2$-H, is added at room temperature or below. The product (XII) may be recovered by crystallization or by extraction into an organic solvent. The reaction of such a naphthoquinone with a secondary cyclic amine ms described by Elslanger et al. in The Journal of Medicinal Chemistry, Volume 13, pages 104–109 (1970). In Step 2, which is a modified Wolff-Kishner reduction, a hydrazine derivative, e.g., the sulfuric acid salt of methoxycarbonylhydrazine, is employed in a non polar solvent such as toluene to produce the substituted hydrazone, represented by graphic formula XIIA. A minor amount of the isomeric compound represented by graphic formula XIIB is also produced. The substituted hydrazone (XIIA) is treated with aqueous base followed by neutralization to produce the $R_2$ substituted naphthol represented by graphic formula IX. The Wolff-Kishner reduction is described in Volume 4 of Organic Reactions published by John Wiley and Sons, New York, Roger Adams editor, Chapter 8 pages 378–422. The very rapid Wolff-Kishner reduction (under mild conditions) of α-carbonyl-hydrazones has been described by Seibert in Chem. Ber. Volume 80 pg 497 (1947). This reaction scheme may also be used to produce acyclic nitrogen containing $R_2$ substituted 2-naphthols.

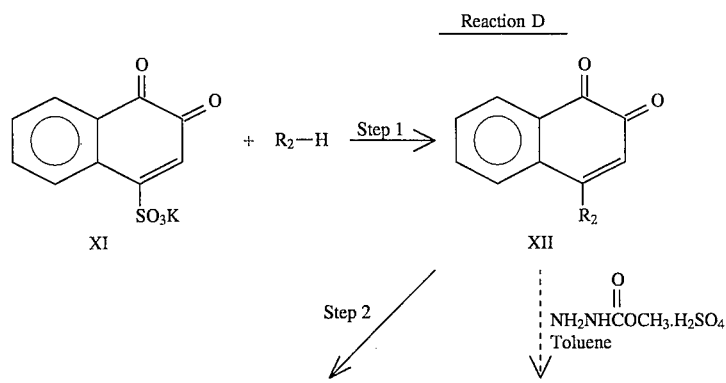

-continued
Reaction D

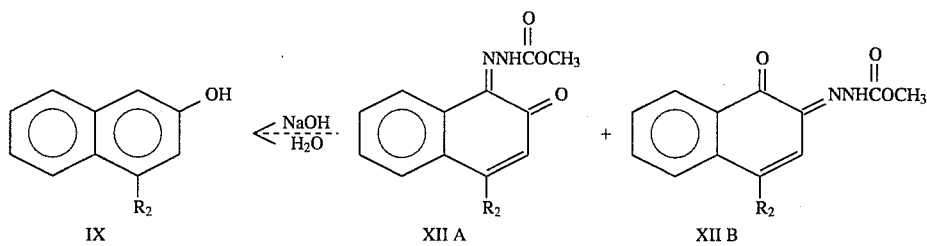

Compounds represented by graphic formula I may be used in those applications in which organic photochromic substances may be employed, such as optical lenses, e.g., vision correcting ophthalmic and plano lenses, face shields, goggles, visors, camera lenses, windows, automotive windshields, aircraft and automotive transparencies, e.g., T-roofs, sidelights, and backlights, plastic films and sheets, textiles and coatings, e.g., coating compositions such as paints, and verification marks on security documents, e.g., documents such as banknotes, passports and drivers' licenses for which authentication or verification of authenticity may be desired. Naphthopyrans represented by graphic formula I exhibit color changes from colorless to colors ranging from yellow to orange.

Examples of contemplated naphthopyrans within the scope of the invention are the following:

(1) 3-(2,2-dimethyl-2,3-dihydrobenzofuran-5-yl)-3 -(4-methoxyphenyl)-6-morpholino-3H-naphtho[2,1-b]pyran;

(2) 3-(2,3-dihydrobenzofuran-5-yl)-3-(4 -methoxyphenyl)-6-piperidino-3H-naphtho[2,1-b]pyran;

(3) 3-(2-methyl-2,3-dihydrobenzofuran-5-yl)-3-(3, 4dimethoxyphenyl)-6-pyrrolidyl-3H-naphtho[2,1-b]pyran;

(4) 3-(1,4-benzodioxan-6-yl)-3-phenyl-6-(1 -indolinyl)-3H-naphtho[2,1-b]pyran;

(5) 3-(1,3-benzodioxol-5-yl)-3-(4-methylphenyl)-6-( 4-methylpiperazin-1-yl)-3H-naphtho[2,1-b]pyran;

(6) 3-(indolin-5-yl) -3-(4-fluorophenyl)-6-(2-methylpiperidino)- 3H-naphtho[2,1-b]pyran;

(7) 3-(2,2,7-trimethyl-2,3-dihydrobenzofuran-5-yl)-3-phenyl-6-(2,6-dimethylmorpholino)-3H-naphtho[2,1-b]pyran;

(8) 3-(2,3-dihydrobenzofuran-5-yl)-3-(4-methoxyphenyl)-6-morpholino-3H-naphtho[2,1-b]pyran;

(9) 3-(2,2-dimethyl-2,3-dihydrobenzofuran-5-yl) -3phenyl-6-pyrrolidyl-3H-naphtho[2,1-b]pyran;

(10) 3-(2-methyl-2,3-dihydrobenzofuran-5-yl)-3-(4-methoxyphenyl)-6-(1-indolinyl)-3H-naphtho[2,1-b]pyran;

(11) 3-(2-methyl-2,3-dihydrobenzofuran-5-yl)-3-(4-methytphenyl)- 6-(3,5-dimethylpiperidino)-3H-naphtho[2,1b]pyran; and

(12) 3-(2-methyl-2,3-dihydrobenzofuran-5-yl)-3-(3,5-dimethoxyphenyl)-( 3,3-dimethylpiperidino)-3H-naphtho[2,1-b]pyran.

The organic photochromic naphthopyrans of graphic formula I may be used in combination with other appropriate complementary organic photochromic materials so that together they produce a desired near neutral gray or brown color shade when the plastic lens containing such photochromic materials are exposed to ultraviolet light. For example, a compound which colors to yellow may be blended with a compound that colors to an appropriate purple to produce a brown shade. Similarly, a compound which is orange in its colored state will produce a shade of gray when used in conjunction with an appropriate blue coloring compound. The aforesaid described combination of photochromic materials may be used also in applications other than ophthalmic lenses.

The novel naphthopyran compounds of the present invention, such as those heretofore described, may be used alone or in combination with complementary photochromic compounds, i.e., organic photochromic compounds having at least one activated absorption maxima within the range of between about 400 and 700 nanometers, or substances containing same, and may be incorporated, e.g., dissolved or dispersed, in a polymeric organic host material used to prepare photochromic articles and which color when activated to an appropriate hue.

A first group of complementary organic photochromic substances contemplated for use with the organic photochromic naphthopyrans of the present invention are those having an activated absorption maximum within the visible range of greater than 570 nanometers, e.g., between about greater than 570 to 700 nanometers. These materials typically exhibit a blue, blueish-green, or blueish-purple color when exposed to ultraviolet light in an appropriate solvent or matrix. Many of such compounds are described in the open literature. For example, spiro(indoline)naphthoxazines have been described, among others, in U.S. Pat. Nos. 3,562,172; 3,578,602; 4,215,010; and 4,342,668; spiro(indoline)naphthoxazines having certain substituents on the 8' and 9' positions of the naphthoxazine portion of the molecule are the subject of copending U.S. patent application Ser. No. 07/993,587, filed Dec. 21, 1992; spiro(indoline)pyridobenzoxazines are described in U.S. Pat. No. 4,637,698; spiro(benzindoline)pyridobenzoxazines and spiro(benzindoline)naphthoxazines are described in U.S. Pat. No. 4,931,219; spiro(benzindoline)naphthopyrans are described in Japanese Patent Publication 62/195383; spiro(indoline)benzoxazines are described in U.S. Pat. No. 4,816,584; spiro(indoline)benzopyrans, spiro(indoline)naphthopyrans, and spirolindoline)quinopyrans are described, for example, in U.S. Pat. No. 4,880,667; and benzopyrans and naphthopyrans having a nitrogen-containing substituent in the 2-position of the pyran ring are described in U.S. Pat. No. 4,818,096. Spiro(indoline)pyrans are also described in the text, *Techniques in Chemistry*, Volume III, "Photochromism," Chapter 3, Glenn H. Brown, Editor, John Wiley and Sons, Inc., New York, 1971.

A second group of complementary organic photochromic substances contemplated for use with the organic photochromic naphthopyrans of the present invention are those having an absorption maximum within the visible range of between about 400 to about 500 nanometers and another absorption maximum within the visible range of between about 500 to about 700 nanometers. These materials typically exhibit color(s) ranging from yellow to purple and yellow/brown to purple/gray when exposed to ultraviolet light in an appropriate solvent or matrix. Examples of these compounds include certain substituted 2H-phenanthro[4,3-b]pyrans; substituted 3H-phenanthro[1,2-b]pyrans; and benzopyran compounds, such as those having substituents at the 2-position of the pyran ring and a substituted or unsubstituted heterocyclic ring, such as a benzothieno or benzofurano ring fused to the benz portion of the benzopyran. Such later described compounds are the subject of co-pending U.S. patent application Ser. No. 08/286,039 filed Aug. 4, 1994 and U.S. Pat. No. 08/201,948, filed Feb. 24, 1994, now abandoned (a later filed continuation-in-part application is now issued as U.S. Pat. No. 5,429,774).

A third group of complementary organic photochromic substances contemplated for use with the organic photochromic naphthopyrans of the present invention are those having at least one absorption maximum within the visible range of between about 400 and less than 500 nanometers. These materials typically exhibit a yellow-orange color when exposed to ultraviolet light in an appropriate solvent or matrix. Such compounds include certain chromenes, i.e., benzopyrans and naphthopyrans. Many of such chromenes are described in the open literature, e.g., U.S. Pat. Nos. 3,567,605; 4,826,977; and 5,066,818. Other examples of complementary benzopyrans and naphthopyrans that may be used with the naphthopyrans of the present invention include: those having a spiro adamantate group at the position alpha to the oxygen atom of the pyran ring, which are described in U.S. Pat. No. 4,826,977; 2H-naphtho-[1,2-b]pyran compounds having certain substitutents at the number 5 and 6 carbon atoms of the naphtho portion of the naphthopyran and at the 2 position of the pyran which are the subject of U.S. Pat. No. 5,458,814; 3H-naphtho[2,1-b] pyrans having at least one ortho-substituted phenyl substituent at the 3-position of the pyran ring which are described in U.S. Pat. No. 5,066,818; 3H-naphtho[2,1-b]pyran compounds having certain substituents at the number 8 carbon atom and certain substituents at the number 7 or 9 carbon atom, all substituents being on the naphtho portion of the naphthopyran, which are the subject of U.S. Pat. No. 5,466,398; 3H-naphtho[2,1-b]pyrans substituted at the 3 position of the pyran ring with (i) an aryl substituent and (ii) a phenyl substituent having a 5- or 6-member heterocyclic ring fused at the number 3 and 4 carbon atoms of the phenyl substituent which are the subject of U.S. Pat. No. 5,384,077; diaryl-3H-naphtho[2,1-b]pyran compounds having a substituted or unsubstituted, 5 or 6 member heterocyclic ring fused to the g, i, or side of the naphthopyran which are the subject of U.S. Pat. No. 5,451,344; naphthopyran compounds substituted at the number 8 carbon atom on the naphtho portion of the naphthopyran ring, with for example, a methoxy group which are the subject of U.S. Pat. No. 5,238,931; naphthopyran compounds, examples of which are 3-aryl- 3-arylalkenyl naphthopyrans, which are described in U.S. Pat. No. 5,274,132; and naphtho[2,1-b]pyrans substituted at the number five carbon atom with, for example, an acetoxy group, which are the subject of U.S. Pat. No. 5,244,602.

Photochromic articles of the present invention may contain one photochromic compound or a mixture of photochromic compounds, as desired or required. Individual photochromic compounds or mixtures of photochromic compounds may be used to attain certain activated colors such as neutral grays or browns.

The compounds of the present invention (hereinafter also referred to and included as a third group photochromic compound) may be used also in combination with the organic photochromic substances of the first complementary group of photochromic compounds described herein, i.e., those that color to colors blue, blueish-green, or blueish-purple with the organic photochromic substances of the second complementary group of photochromic compounds described herein that exhibit colors ranging from yellow to purple and yellow/brown to purple/gray and/or with other organic photochromic substances of the third complementary group of photochromic compounds described herein that exhibit the colors yellow/orange.

Each of the photochromic substances described herein may be used in amounts (or in a ratio) such that an organic host material to which the photochromic compounds or mixture of compounds is applied or in which they are incorporated exhibits a desired resultant color, e.g., a substantially neutral color when activated with unfiltered sunlight, i.e., as near a neutral color as possible given the colors of the activated photochromic compounds.

A neutral gray color exhibits a spectrum that has relatively equal absorption in the visible range between 400 and 700 nanometers. A neutral brown color exhibits a spectrum in which the absorption in the 400–550 nanometer range is moderately larger than in the 550–700 nanometer range. An alternative way of describing color is in terms of its chromaticity coordinates, which describe the qualities of a color in addition to its luminance factor, i.e., its chromaticity. In the CIE system, the chromaticity coordinates are obtained by taking the ratios of the tristimulus values to their sum, e.g., $x=X/(X+Y+Z)$ and $y=Y/(X+Y+Z)$. Color as described in the CIE system can be plotted on a chromaticity diagram, usually a plot of the chromaticity coordinates x and y. See pages 47–52 of *Principles of Color Technology*, by F. W. Billmeyer, Jr., and Max Saltzman, Second Edition, John Wiley and Sons, N.Y. (1981). As used herein, a near neutral color is one in which the chromaticity coordinate values of "x" and "y" for the color are within the following ranges (D65 illuminant): $x=0.260$ to $0.400$, $y=0.280$ to $0.400$ following activation to 40 percent luminous transmission by exposure to solar radiation (Air Mass 1 or 2).

The amount of photochromic substance or composition containing same applied to or incorporated into a host material is not critical provided that a sufficient amount is used to produce a photochromic effect discernible to the naked eye upon activation. Generally such amount can be described as a photochromic amount. The particular amount used depends often upon the intensity of color desired upon irradiation thereof and upon the method used to incorporate or apply the photochromic substances. Typically, the more photochromic substance applied or incorporated, the greater is the color intensity up to a certain limit.

The relative amounts of the aforesaid photochromic compounds used will vary and depend in part upon the relative intensities of the color of the activated species of such compounds, and the ultimate color desired. Generally, the amount of total photochromic substance incorporated into or applied to a photochromic optical host material may range from about 0.05 to about 1.0, e.g., from 0.1 to about 0.45, milligrams per square centimeter of surface to which the photochromic substance(s) is incorporated or applied. When mixtures of the aforedescribed organic photochromic complementary groups are used, the weight ratio of such materials, i.e., (first to third), (second to third), and (naphthopyran of the present invention to other third group compounds) will vary from about 1:3 to about 3:1, e.g., between about 0.75:1 and about 2:1. The combination of the first, second, and third described organic photochromic complementary groups may have a weight ratio that will vary from about 1:3:1 to 3:1:3.

The photochromic substances of the present invention may be applied to or incorporated into a host material such as a polymeric organic host material by various methods described in the art. Such methods include dissolving or dispersing the photochromic substance within the host material, e.g., casting it in place by adding the photochromic substance to the monomeric host material prior to polymerization; imbibition of the photochromic substance into the host material by immersion of the host material in a hot solution of the photochromic substance or by thermal transfer; providing the photochromic substance as a separate layer between adjacent layers of the host material, e.g., as a part of a polymeric film; and applying the photochromic substance as part of a coating placed on the surface of the hose material. The term "imbibition" or "imbibe" is intended to mean and include permeation of the photochromic substance alone into the host material, solvent assisted transfer of the photochromic substance into a porous polymer, vapor phase transfer, and other such transfer mechanisms.

Compatible (chemically and color-wise) tints, i.e., dyes, may be applied to the host material to achieve a more aesthetic result, for medical reasons, or for reasons of fashion. The particular dye selected will vary and depend on the aforesaid need and result to be achieved. In one embodiment, the dye may be selected to complement the color resulting from the activated photochromic substances, e.g., to achieve a more neutral color or absorb a particular wavelength of incident light. In another embodiment, the dye may be selected to provide a desired hue to the host matrix when the photochromic substances is in an unactivated state.

Adjuvant materials may also be incorporated into the host material with the photochromic substances prior to, simultaneously with or subsequent to application or incorporation of the photochromic substances in the host material. For example, ultraviolet light absorbers may be admixed with photochromic substances before their application to the host material or such absorbers may be superposed, e.g., superimposed, as a layer between the photochromic substance and the incident light. Further, stabilizers may be admixed with the photochromic substances prior to their application to the host material to improve the light fatigue resistance of the photochromic substances. Stabilizers, such as hindered amine light stabilizers and singlet oxygen quenchers, e.g., a nickel ion complex with an organic ligand, are contemplated. They may be used alone or in combination. Such stabilizers are described in U.S. Pat. No. 4,720,356. Finally, appropriate protective coating(s) may be applied to the surface of the host material. These may be abrasion resistant coatings and/or coatings that serve as oxygen barriers. Such coatings are known in the art.

The foregoing singlet oxygen quenchers and hindered amine light stabilizers may be used singly or in combination in amounts sufficient to enhance the light-fatigue resistance of the photochromic substance(s) described herein. Between 0.01 and about 5 percent by weight of the foregoing stabilizers may be used (alone or in combination) to improve the light fatigue resistance of the photochromic materials.

The host material will usually be transparent, but may be translucent or even opaque. The host material need only be transparent to that portion of the electromagnetic spectrum, which activates the photochromic substance, i.e., that wavelength of ultraviolet (I/V) light that produces the open form of the substance and that portion of the visible spectrum that includes the absorption maximum wavelength of the substance in its UV activated form, i.e., the open form. Preferably, the host color should not be such that it masks the color of the activated form of the photochromic substance, i.e., so the change in color is readily apparent to the observer. More preferably, the host material article is a solid transparent or optically clear material, e.g., materials suitable for optical applications, such as plano and ophthalmic lenses, windows, automotive transparencies, e.g., windshields, aircraft transparencies, plastic sheeting, polymeric films, etc.

Examples of polymeric organic host materials which may be used with the photochromic substances or compositions described herein include: polymers, i.e., homopolymers and copolymers, of polyol(allyl carbonate) monomers, diethylene glycol dimethacrylate monomers, diisopropenyl benzene monomers, and alkoxylated polyhydric alcohol acrylate monomers such as ethoxylated trimethylol propane triacrylate monomers; polymers, i.e., homopolymers and copolymers, of polyfunctional, i.e., mono-, di-, tri-, tetra, or multi-functional, acrylate and/or methacrylate monomers, polyacrylates, polymethacrylates, poly($C_1$–$C_{12}$ alkyl methacrylates) such as poly(methyl methacrylate), polyoxy(alkylene methacrylates) such as poly(ethylene glycol bis methacrylates), poly(alkoxylated phenol methacrylates) such as poly(ethoxylated bisphenol A dimethacrylate), cellulose acetate, cellulose triacetate, cellulose acetate propionate, cellulose acetate butyrate, poly(vinyl acetate), poly(vinyl alcohol), poly(vinyl chloride), poly(vinylidene chloride), polyurethanes, thermoplastic polycarbonates, polyesters, poly(ethylene terephthalate), polystyrene, poly (alpha methylstyrene), copoly(styrene-methyl methacrylate), copoly(styrene-acrylonitrile), polyvinylbutyral and polymers, i.e., homopolymers and copolymers, of diallylidene pentaerythritol, particularly copolymers with polyol (allyl carbonate) monomers, e.g., diethylene glycol bis(allyl carbonate), and acrylate monomers.

Transparent copolymers and blends of transparent polymers are also suitable as host materials. Preferably, the host material is an optically clear polymerized organic material prepared from a thermoplastic polycarbonate resin, such as the carbonate-linked resin derived from bisphenol A and phosgene, which is sold under the trademark, LEXAN; a polyester, such as the material sold under the trademark, MYLAR; a poly(methyl methacrylate), such as the material sold under the trademark, PLEXIGLAS; polymerizates of a polyol(allyl carbonate) monomer, especially diethylene glycol bis(allyl carbonate), which monomer is sold under the trademark CR-39, and polymerizates of copolymers of a polyol (allyl carbonate), e.g., diethylene glycol bis(allyl carbonate), with other copolymerizable monomeric materials, such as copolymers with vinyl acetate, e.g., copolymers of from 80–90 percent diethylene glycol bis(allyl carbonate) and 10–20 percent vinyl acetate, particularly 80–85 percent of the bis(allyl carbonate) and 15–20 percent vinyl acetate, and copolymers with a polyurethane having terminal diacrylate functionality, as described in U.S. Pat. Nos. 4,360,653 and 4,994,208; and copolymers with aliphatic urethanes, the terminal portion of which contain allyl or acrylyl functional groups as described in U.S. Pat. No. 5,200,483; poly(vinyl acetate), polyvinylbutyral, polyurethane, polymers of members of the group consisting of diethylene glycol dimethacrylate monomers, diisopropenyl benzene monomers, and ethoxylated trimethylol propane triacrylate monomers; cellulose acetate, cellulose propionate, cellulose butyrate, cellulose acetate butyrate, polystyrene and copolymers of styrene with methyl methacrylate, vinyl acetate and acrylonitrile. More particularly, contemplated is use of the photochromic naphthopyrans of the present invention with optical organic resin monomers used to produce optically clear polymerizates, i.e., materials suitable for optical applications, such as for example plano and ophthalmic lenses, windows, and automotive transparencies. Such optically clear polymerizates may have a refractive index that may range from about 1.48 to about 1.75, e.g., from about 1.495 to about 1.66.

The present invention is more particularly described in the following example which is intended as illustrative only, since numerous modifications and variations therein will be apparent to those skilled in the art.

EXAMPLE

Step 1

5-(4-methoxybenzoyl)-2-methyl-2,3-dihydrobenzofuran (72.0 grams, 0.27 mole) was dissolved in a reaction flask containing 300 milliliters (mL) of anhydrous tetrahydrofuran saturated with acetylene and stirred at room temperature. An 18 weight percent suspension of sodium acetylide in xylene/mineral oil (0.3 mole of sodium acetylide) was added to the reaction flask and the mixture was stirred. After 16 hours at room temperature under a nitrogen atmosphere, the contents of the reaction flask were added to a 5 weight percent aqueous hydrochloric acid and ice mixture. The resulting mixture was extracted with diethyl ether. The organic layer was separated, washed with water, and dried over anhydrous sodium sulfate. The solvents, diethyl ether and tetrahydrofuran, were removed under vacuum to yield an oily product containing 1-(4-methoxyphenyl)-1-(2-methyl-2,3-dihydrobenzofur- 5-yl)-2-propyn-1-ol, which was not purified further but used directly in Step 5.

Step 2

1,2-naphthoquinone-4-sulfonic acid, potassium salt (25 grams, 0.09 mole) was added to a reaction flask containing 75 mL of water. The resulting slurry was cooled in an ice bath while morpholine (10 grams, 0.12 mole) was added dropwise. After a brick-red colored mixture formed, the contents of the flask were allowed to warm to room temperature and the solid product was collected by filtration. The solid was washed with a few mL of cold water and air dried. The yield of product, 4-morpholino-1,2-naphthoquinone, which had a melting point of 196°–198° C. was 12 grams.

Step 3

4-morpholino-1,2-naphthoquinone (3.0 grams) and the sulfuric acid salt of methoxycarbonylhydrazine 3.0 grams) were added to a reaction flask containing 75 mL of toluene. The sulfuric acid salt of methoxycarbonylhydrazlne was prepared by adding an excess of sulfuric acid to an ethanol solution of methoxycarbonylhydrazine in a dropwise fashion, filtering and drying the resulting precipitate. The contents of the reaction flask were stirred at room temperature for 48 hours. The resulting yellow colored solid was filtered and washed with toluene to remove a small amount of the red colored minor product 4-morpholino-1,2-naphthoquinone-2-methoxycarbonyl-hydrazone. The yield of the major product, 4-morpholino- 1,2-naphthoquinone-1-methoxycarbonylhydrazone, which had a melting point of 188°–190° C., was 2.0 grams.

Step 4

4-morpholino-1,2-naphthoquinone-1-methoxycarbonyl-hydrazone (2.0 grams) was added to a reaction flask containing 50 mL of a 5 weight percent aqueous sodium hydroxide solution. The mixture was heated on a steam bath for 30 minutes. The resulting solution was filtered to remove undissolved material. The pH of the liltrate was adjusted to 8 by the addition of dilute hydrochloric acid and the resulting precipitate was collected by filtration and dried. The yield of crystalline product, 4-morpholino-2-naphthol, which had a melting point of 198°–200° C. was 1.5 grams.

Step 5

1-(4-methoxyphenyl)-1-(2-methyl-2,3-dihydrobenzofur-5-yl)-2-propyn-1-ol (1.5 grams) from Step 1 and 4-morpholino- 2-naphthol (1.5 grams) from Step 4 were added to a reaction flask containing 100 mL of toluene and stirred. A catalytic amount of p-toluenesulfonic acid (about 2 drops) was added, and the mixture was heated to 50° C. and stirred for 2 hours. Afterwards, the reaction mixture was cooled and poured into a 5 weight percent sodium hydroxide solution. The organic layer was separated, washed with water, and the solvent, toluene, was removed under vacuum. The resulting residue was purified using a silica gel column and a 2:1 mixture of hexane: ethyl acetate as the eluant. The photochromic fractions were combined and the eluant was removed under vacuum. The resulting product was induced to crystallize from a mixture of diethyl ether and hexane. The recovered crystals, 0.5 grams, had a melting point of 185°–187° C. A nuclear magnetic resonance (NMR) spectrum showed the product to have a structure consistent with 3-(2-methyl-2,3-dihydrobenzofuran-5-yl)- 3-(4-methoxyphenyl)-6-morpholino-[3H]-naphtho[2,1-b]pyran.

The naphthopyran prepared in the Example was dissolved in diethylene glycol dimethyl ether. The concentration of the resulting solution was approximately 0.5 milligram per milliliter. The solution was tested in a UV visible spectrophotometer to determine the K max, i.e., the wavelength in the visible spectrum at which the greatest absorption of the photochromic compound occurs. The λ max of the Example compound was determined to be 460 nanometers.

Although the present invention has been described with reference to the specific details of particular embodiments thereof, it is not intended that such details be regarded as limitations upon the scope of the invention except insofar as to the extent that they are included in the accompanying claims.

We claim:

1. A naphthopyran compound represented by the following graphic formula:

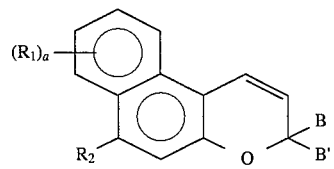

wherein, (a) $R_1$ is $C_1$–$C_{10}$ alkyl, halogen, or the group, —O—L, wherein L is $C_1$–$C_{12}$ alkyl, said halogen being chloro, fluoro, or bromo; and a is the integer 0, 1, or 2;

(b) $R_2$ is selected from the group consisting of saturated, unsubstituted, mono-substituted, and di-substituted nitrogen-containing heterocyclic groups represented by the following graphic formulae:

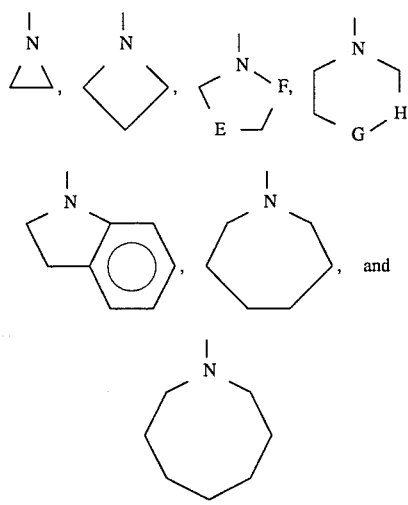

wherein E and F are each nitrogen or carbon atom, G is nitrogen, oxygen, or carbon atom, and H is nitrogen or carbon, provided that when E is nitrogen, F is carbon, and when H is nitrogen, G is carbon, and said nitrogen-containing heterocyclic group substitutents being selected from $C_1$–$C_6$ alkyl and $C_1$–$C_6$ alkoxy;

(c) B is the substituted or unsubstituted aryl group, naphthyl or phenyl, said aryl substituents being $C_1$–$C_5$ alkyl, halo($C_1$–$C_5$)alkyl, hydroxy, $C_1$–$C_5$ alkoxy, $C_1$–$C_4$ alkoxy($C_1$–$C_4$)alkyl, halogen, morpholino, piperidino, or R(R')N—, wherein R and R' are each hydrogen or $C_1$–$C_3$ alkyl, said halogen (or halo) groups being fluorine or chlorine; and (d) B' is selected from the groups represented by the following graphic formulae:

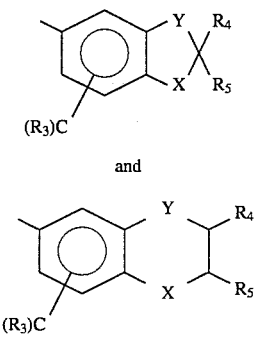

wherein X is oxygen or nitrogen and Y is carbon or oxygen provided that when X is nitrogen, Y is carbon; $R_4$ and $R_5$ are each hydrogen or $C_1$–$C_5$ alkyl; each $R_3$ is $C_1$–$C_5$ alkyl, $C_1$–$C_5$ alkoxy, hydroxy, or halogen, said halogen being chloro, fluoro, or bromo, and c is an integer from 0 to 3.

2. The naphthopyran of claim 1 wherein:

(a) $R_1$ is $C_1$–$C_5$ alkyl, fluoro, bromo, or the group —O—L, wherein L is $C_1$–$C_4$ alkyl, and a is the integer 0 or 1;

(b) $R_2$ is an unsubstituted or mono-substituted member of the group consisting of indolinyl, morpholino, and piperidino;

(c) B is represented by the following graphic formula:

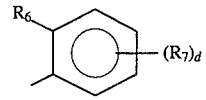

wherein $R_6$ is hydrogen, $C_1$–$C_4$ alkyl, $C_1$–$C_4$ alkoxy, fluoro, or chloro, each $R_7$ is a $C_1$–$C_4$ alkyl, $C_1$–$C_4$ alkoxy, hydroxy, chloro or fluoro, and d is an integer from 0 to 2; and (d) B' is selected from the groups represented by the following graphic formulae:

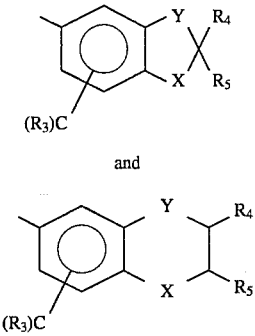

wherein X is oxygen, Y is carbon or oxygen, $R_4$ and $R_5$ are each hydrogen or $C_1$–$C_4$ alkyl, each $R_3$ is a $C_1$–$C_4$ alkyl, $C_1$–$C_4$ alkoxy, hydroxy, or fluoro, and c is an integer from 0 to 2.

3. The naphthopyran compound of claim 2 wherein $R_1$ is $C_1$–$C_3$ alkyl, fluorine or the group —O—L, wherein L is methyl, $R_2$ is morpholino; and $R_6$ is hydrogen; $R_7$ is selected from the group consisting of fluoro, methyl and methoxy; B' is 2,3-dihydrobenzofuran-5-yl, 2-methyldihydrobenzofuran-5-yl, indoline-5-yl, 1,2,3,4-tetrahydroquinoline-6-yl, chroman-6-yl, or 1,3-benzodioxole-5-yl; and a, and d are the integers 0 or 1.

4. A naphthopyran compound selected from the group consisting of:

(a) 3-(1,4-benzodioxan-6-yl)-3-phenyl-6-(1-indolinyl)-3H-naphtho[2,1-b]pyran;

(b) 3-(2-methyl-2,3-dihydrobenzofuran-5-yl)-3-(4-methoxyphenyl)-6-morpholino-[3H]-naphtho[2,1-b]pyran; and (c) 3-(2,3-dihydrobenzofuran-5-yl)-3-(4-methoxyphenyl)-6-piperidino-3H-naphtho[2,1-b]pyran;

5. A photochromic article comprising a polymeric organic host material and a photochromic amount of a naphthopyran compound of claim 1.

6. The photochromic article of claim 5 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

7. The photochromic article of claim 6 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

8. The photochromic article of claim 7 wherein the photochromic compound is present in an amount of from about 0.05 to 1.0 milligram per square centimeter of organic host material surface to which the photochromic substance(s) is incorporated or applied.

9. The photochromic article of claim 8 wherein the article is a lens.

10. A photochromic article comprising a photochromic amount of the naphthopyran compound of claim 2 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

11. A photochromic article comprising a photochromic amount of the naphthopyran compound of claim 3 and a polymeric organic host material selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

12. A photochromic article comprising, in combination, a photochromic amount of each of (a) at least one naphthopyran compound of claim 1, and (b) at least one other organic photochromic compound having at least one activated absorption maxima within the range of between about 400 and 700 nanometers and a polymeric organic host material selected from the group consisting of poly(methyl methacrylate), poly(ethylene glycol bis methacrylate), poly-(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, diisopropenyl benzene monomers, and ethoxylated trimethylol propane triacrylate monomers.

13. A photochromic article comprising, in combination, a solid transparent polymeric organic host material, and a photochromic amount of each of (a) at least one naphthopyran compound of claim 2, and (b) at least one other organic photochromic compound having at least one activated absorption maxima within the range of between about 400 and 700 nanometers.

14. The photochromic article of claim 13 wherein the polymeric organic host material is selected from the group consisting of polyacrylates, polymethacrylates, poly($C_1$–$C_{12}$ alkyl methacrylates), polyoxy(alkylene methacrylates), poly(alkoxylated phenol methacrylates), cellulose acetate, cellulose triacetate, cellulose acetate propionate, cellulose acetate butyrate, poly(vinyl acetate), poly(vinyl alcohol), poly(vinyl chloride), poly(vinylidene chloride), thermoplastic polycarbonates, polyesters, polyurethanes, poly(ethylene terephthalate), polystyrene, poly(alpha methylstyrene), copoly(styrene-methylmethacrylate), copoly(styrene-acrylonitrile), polyvinylbutyral and polymers of members of the group consisting of polyol(allyl carbonate) monomers, polyfunctional acrylate monomers, polyfunctional methacrylate monomers, diethylene glycol dimethacrylate monomers, diisopropenyl benzene monomers, alkoxylated polyhydric alcohol acrylate monomers and diallylidene pentaerythritol monomers.

15. The photochromic article of claim 14 wherein the organic photochromic compound (b) is selected from the group consisting of:
(a) organic photochromic substances having at least one absorption maximum in the visible range of between 400 and less than 500 nanometers;
(b) organic photochromic substances having an absorption maximum within the visible range of between about 400 and 500 nanometers and an absorption maximum within the visible range of between 500 and 700 nanometers; and
(c) organic photochromic substances having an activated absorption maxima in the visible range of greater than 570 nanometers; and
(d) mixtures of said organic photochromic substances.

16. The photochromic article of claim 15 wherein the polymeric organic host material is a solid transparent homopolymer or copolymer selected from the group consisting of poly(methyl methacrylate), poly(ethylene glycol bis methacrylate), poly(ethoxylated bisphenol A dimethacrylate), thermoplastic polycarbonate, poly(vinyl acetate), polyvinylbutyral, polyurethane and polymers of members of the group consisting of diethylene glycol bis-(allyl carbonate) monomers, diethylene glycol dimethacrylate monomers, diisopropenyl benzene monomers, and ethoxylated trimethylol propane triacrylate monomers.

17. The photochromic article of claim 13 wherein the organic photochromic compound (b) is selected from the group consisting of spiro(indoline)naphthoxazines, spiro(indoline)-pyridobenzoxazines, spiro(benzindoline)pyridobenzoxazines, spiro(benzindoline)naphthoxazines, spiro(benzindoline)naphthopyrans, spiro(indoline)benzoxazines, spiro(indoline)-benzopyrans, spiro(indoline)naphthopyrans, spiro(indoline)-quinopyrans, spiro(indoline)pyrans, 3H-naphtho[2,1-b]pyrans, 2H-phenanthro[4,3-b]pyrans; 3H-phenanthro[1,2-b]pyrans; benzopyran compounds and mixtures of such photochromic substances.

18. A photochromic article comprising, in combination, a photochromic amount of each of (a) at least one naphthopyran compound of claim 3, and (b) at least one other organic photochromic compound having at least one activated absorption maxima within the range of between about 400 and 700 nanometers and a polymeric organic host material selected from the group consisting of poly(methyl methacrylate), poly(ethylene glycol bis methacrylate), poly-(ethoxylated bisphenol A dimethacrylate), thermoplastic polycarbonate, poly(vinyl acetate), polyvinylbutyral, polyurethane and polymers of members of the group consisting of diethylene glycol bis(allyl carbonate) monomers, diethylene glycol dimethacrylate monomers, diisopropenyl benzene monomers, and ethoxylated trimethylol propane triacrylate monomers.

19. A photochromic article comprising a polymerizate of an optical organic resin monomer and a photochromic amount of tile naphthopyran compound of claim 1.

20. The photochromic article of claim 19 wherein the refractive index of the polymerizate is from about 1.48 to about 1.75.

21. The photochromic article of claim 20 wherein the refractive index of the polymerizate is from about 1.495 to about 1.66.

* * * * *